United States Patent
Lee

(10) Patent No.: US 10,709,450 B2
(45) Date of Patent: Jul. 14, 2020

(54) BLOOD VESSEL CONNECTING APPARATUS

(71) Applicant: KOREA INSTITUTE OF MACHINERY & MATERIALS, Daejeon (KR)

(72) Inventor: Yongkoo Lee, Daegu (KR)

(73) Assignee: KOREA INSTITUTE OF MACHINERY & MATERIALS, Daejeon (KR)

(*) Notice: Subject to any disclaimer, the term of this patent is extended or adjusted under 35 U.S.C. 154(b) by 163 days.

(21) Appl. No.: 14/966,957

(22) Filed: Dec. 11, 2015

(65) Prior Publication Data
US 2017/0119393 A1    May 4, 2017

(30) Foreign Application Priority Data
Oct. 13, 2015   (KR) .................. 10-2015-0143038

(51) Int. Cl.
*A61B 17/11*      (2006.01)
*A61B 17/064*     (2006.01)

(52) U.S. Cl.
CPC ....... *A61B 17/11* (2013.01); *A61B 2017/0649* (2013.01); *A61B 2017/1107* (2013.01); *A61B 2017/1135* (2013.01)

(58) Field of Classification Search
CPC .... A61B 2017/1135; A61B 2017/1139; A61B 17/115; A61B 17/11; A61B 2017/0649; A61B 2017/1107
See application file for complete search history.

(56) References Cited

U.S. PATENT DOCUMENTS

| | | | |
|---|---|---|---|
| 5,904,697 A * | 5/1999 | Gifford, III | A61B 17/064 606/153 |
| 6,746,459 B2 | 6/2004 | Kato | |
| 2004/0050393 A1* | 3/2004 | Golden | A61B 17/0482 128/898 |
| 2004/0176786 A1* | 9/2004 | Edoga | A61B 17/115 606/153 |
| 2005/0070924 A1* | 3/2005 | Schaller | A61B 17/11 606/142 |
| 2009/0264985 A1* | 10/2009 | Bruszewski | A61F 2/90 623/1.18 |
| 2013/0282026 A1* | 10/2013 | Hoarau | A61B 17/11 606/142 |

FOREIGN PATENT DOCUMENTS

JP    2003111764 A    4/2003
JP      4583881 B2   11/2010

* cited by examiner

*Primary Examiner* — Kathleen S Holwerda
*Assistant Examiner* — Brooke Labranche
(74) *Attorney, Agent, or Firm* — Hauptman Ham, LLP

(57) ABSTRACT

A blood vessel connecting apparatus connects a first blood vessel to a second blood vessel. The blood vessel connecting apparatus includes an elastic connection part and a fixing part. The elastic connection part has an elastic restoring force, is inserted in an end of the second blood vessel and extends along an extending direction of the second blood vessel. The fixing part fixes the elastic connection part to an inside of the second blood vessel.

12 Claims, 6 Drawing Sheets

BLOOD VESSEL CONNECTING APPARATUS

PRIORITY STATEMENT

This application claims priority under 35 U.S.C. § 119 to Korean Patent Application No. 10-2015-0143038, filed on Oct. 13, 2015, and all the benefits accruing therefrom, the content of which is herein incorporated by reference in its entirety.

BACKGROUND

1. Field of Disclosure

The present disclosure of invention relates to a blood vessel connecting apparatus. More particularly, the present disclosure of invention relates to a blood vessel connecting apparatus connecting blood vessels with each other.

2. Description of Related Technology

According to an elderly society and westernized food life, a population of patients suffering from angiosis and an age range of the patients are annually increasing. Coronary artery bypass surgery and bypass surgery using artificial blood vessel are generally used to treat the angiosis, and the surgery is normally performed by a suture.

However, the surgery is risky and requires highly skilled surgery as long as the suture is used while the patient's heart is intentionally in cardiac attest.

In addition, a need for a surgery connecting blood vessels with each other without intentional cardiac attest increases because bleeding at the blood vessels occurs during the process of the intentional cardiac attest and rehabilitating the heart.

Related to the surgery connecting blood vessels with each other, Japanese laid-open application No. 2003-111764 discloses an invention of pulling a blood vessel to a hanger part and pressing the blood vessel via a pressure device. Japanese granted patent No. 4583881 discloses an invention of connecting blood vessels each other via sealing device. However, in case of the above-mentioned inventions, it is hard to solve foregoing problems because it takes long time to connect blood vessels with each other via the method disclosed in the above-mentioned inventions.

Thus, a blood vessel connecting device without the suture is needed for decreasing the surgery time.

SUMMARY

The present invention is developed to solve the above-mentioned problems of the related arts. The present invention provides to an apparatus capable of rapidly connecting blood vessels with each other via an elasticity of an elastic connection part to increase stability of a surgery.

According to an example embodiment, a blood vessel connecting apparatus connects a first blood vessel to a second blood vessel. The blood vessel apparatus includes an elastic connection part and a fixing part. The elastic connection part has an elastic restoring force, is inserted in an end of the second blood vessel and extends along an extending direction of the second blood vessel. The fixing part fixes the elastic connection part to an inside of the second blood vessel.

In an example embodiment, the fixing part may fix the elastic connection part such that the elastic connection part is spaced apart from one another at a predetermined distance along the perimeter of the second blood vessel.

In an example embodiment, the elastic connection part may simultaneously moves toward the first blood vessel and bends via the elastic restoring force such that the elastic connection part connects the first blood vessel to the second blood vessel when the fixing part is partially detached from the elastic connection part.

In an example embodiment, the elastic connection part may simultaneously pass through the first and second blood vessels and bend so that the first and second blood vessels are twisted with each other.

In an example embodiment, the elastic connection part may include a first support unit and a second support unit. The first support unit may be inserted into the second blood vessel. The second support unit may extend from the first support unit to an end of the second blood vessel. The end of the second support unit extending from the first support unit may sharply form to pass through the first and second blood vessels.

In an example embodiment, the fixing part may include a first temporary fixing unit and a first guide unit. The first temporary fixing unit may temporarily fix the first support unit. The first guide unit may be fixed inside of the second blood vessel and formed between the second blood vessel and the second support unit.

In an example embodiment, the first support unit and the second support unit may simultaneously move forward the end of the second blood vessel and bend such that the first support unit and the second support unit connect the first blood vessel to the second blood vessel when the first temporary fixing unit is detached from the elastic connection part.

In an example embodiment, the fixing part may include a second guide unit and a second temporary fixing unit. The second guide unit may have a cylindrical shape. A first end of the second guide unit may be inserted into the second blood vessel and a second end of the second guide unit may be exposed at the end of the second blood vessel to fix the first support unit. A second temporary fixing unit may be formed at the first end of the second guide unit and fix the first support unit.

In an example embodiment, the second guide unit may include an inserting part.

The inserting part may extend from the first end of the second guide unit to the second end of the second guide unit. The first support unit may be inserted into the inserting part and make closely contact with the inserting part.

In an example embodiment, the first support unit and the second support unit may pass through the first blood vessel or the second blood vessel and bend to outside of the second blood vessel to connect the first blood vessel to the second blood vessel when the second temporary fixing unit is detached from the first support unit.

In an example embodiment, each of the first and the second blood vessels may be one of an artificial blood vessel and a vital blood vessel.

According to the example embodiments of the present invention, the blood vessel connecting apparatus is inserted into an first end of the second blood vessel and a portion of the first end of the second blood vessel is inserted into an inside of the first blood vessel. Then, the first support unit and the second support unit quickly bend to the outside of the end of the second blood vessel, and the first support unit moves toward the first blood vessel, when the first temporary fixing unit is removed. Thus, an elasticity of the first support unit and the second support unit provides force to connect the second blood vessel to the first blood vessel. In addition, side-effects of the surgery may be reduced and the blood vessel connecting apparatus doesn't require relatively high skill for use.

In addition, the first blood vessel and the second blood vessel are connected and twisted with each other and a contact area between the first blood vessel and the second blood vessel increases, so that the contact area prevents a blood from leaking out from the first blood vessel and the second blood vessel and a binding force between the first blood vessel and the second blood vessel increases via an elasticity of the second support unit 220.

In addition, the first guide unit is arranged between the first support unit and the second blood vessel and prevents the elastic connection part from bending drastically and from moving to an unintended direction, when the first temporary fixing unit is removed and the first support unit and the second support unit simultaneously bend.

In addition, the inserting part makes contact with the first support unit to guide the second support unit to bend toward the outside of the end of the second blood vessel and a plurality of the second support units is spaced apart from each other at a predetermined distance, so that the first blood vessel is strongly connected with the second blood vessel.

In addition, the shape of the inserting part may be changed depending on the shape of the elastic connection part or the condition of the first blood vessel and the second blood vessel, and may minimize the wound of the first blood vessel and the second blood vessel.

BRIEF DESCRIPTION OF THE DRAWINGS

The above and other features and advantages will become more apparent by describing exemplary embodiments thereof with reference to the accompanying drawings, in which.

DETAILED DESCRIPTION

Hereinafter, exemplary embodiment of the invention will be explained in detail with reference to the accompanying drawings.

Figure 1:
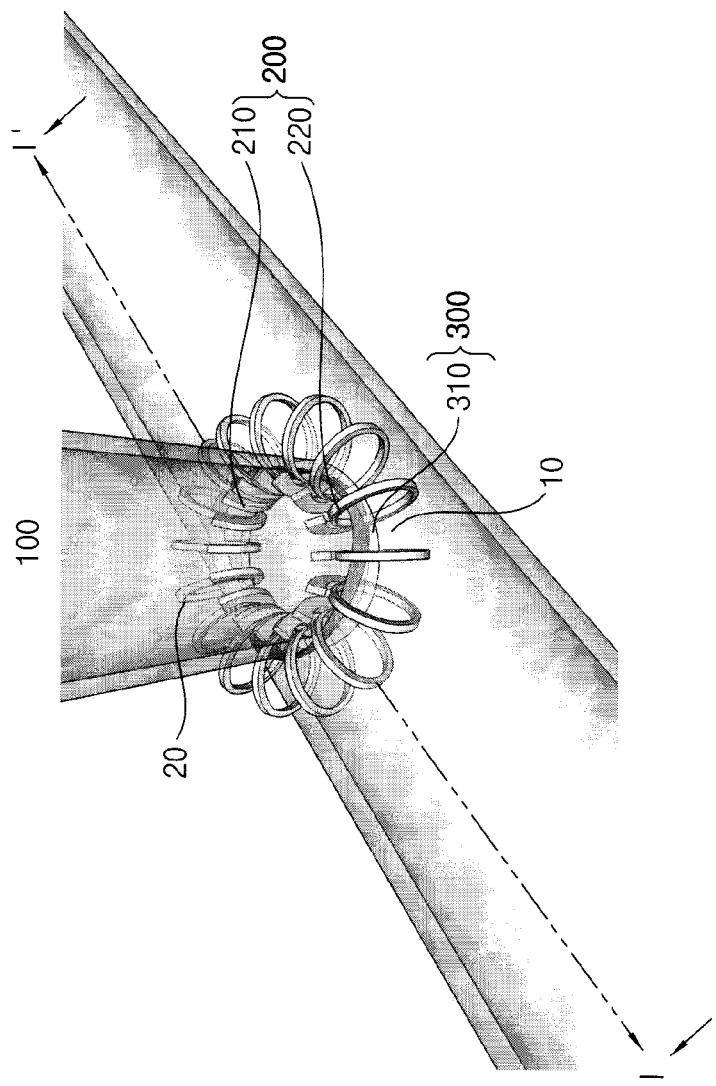
FIG. 1 is a perspective view illustrating a blood vessel connecting apparatus connecting first and second blood vessels with each other according to an example embodiment of the present invention.
Figure 2:
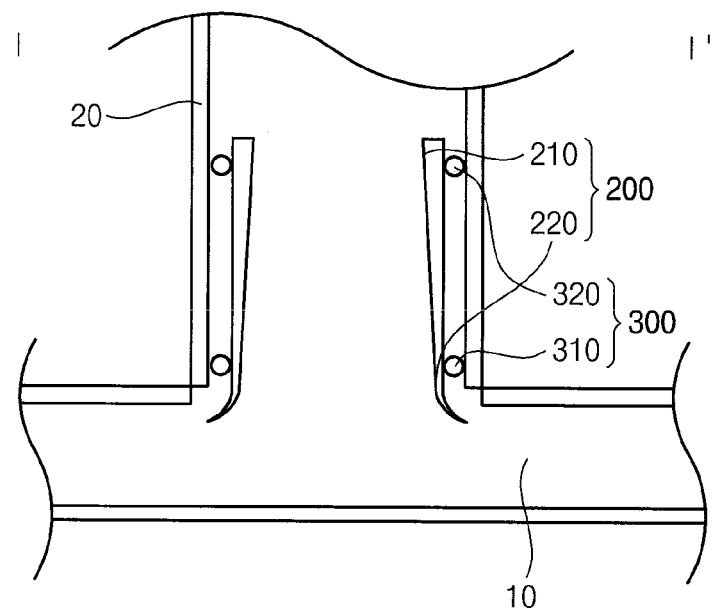
FIGS. 2 to 4 are cross-sectional views taken along a line of I-I' of FIG. 1, illustrating steps of connecting the blood vessels via the blood vessel apparatus of FIG. 1.
Figure 3:
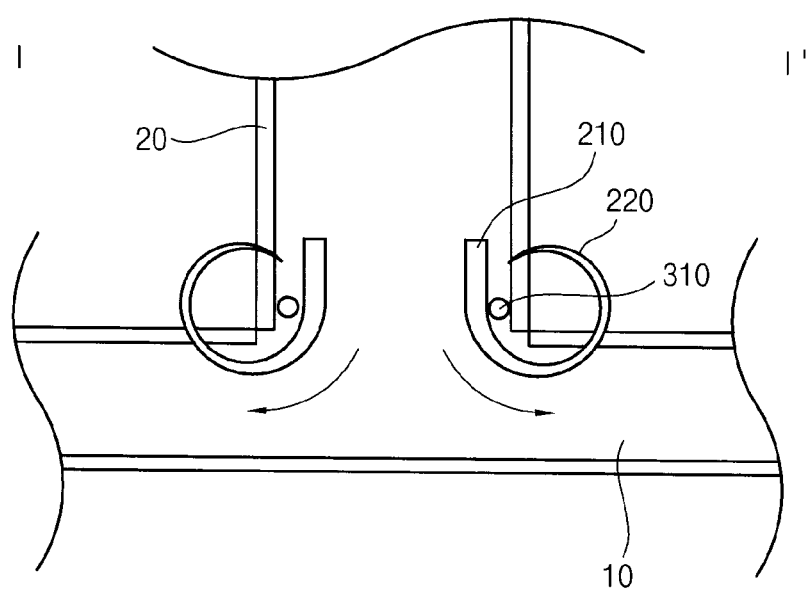
Figure 4:
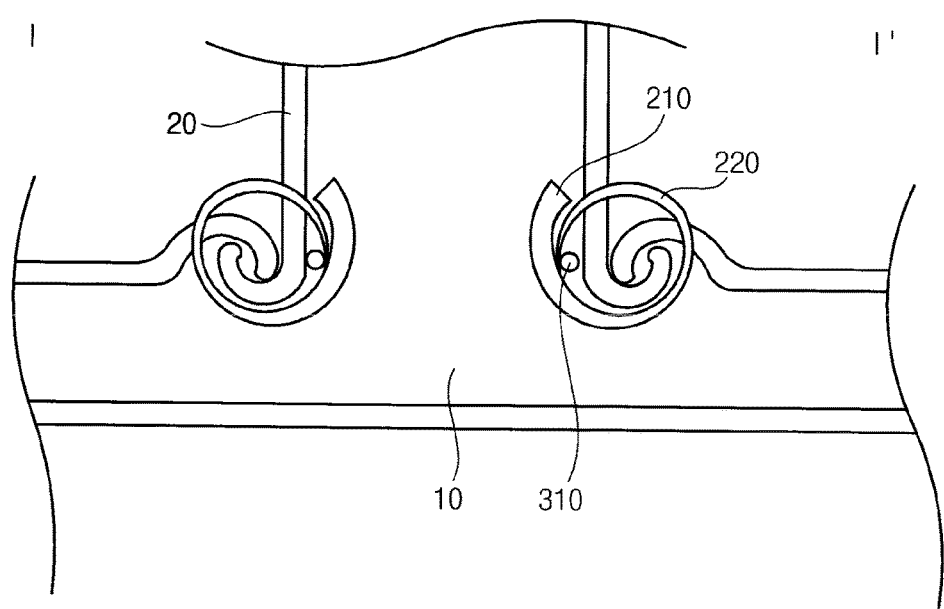

FIG. 1 is a perspective view illustrating a blood vessel connecting apparatus connecting first and second blood vessels with each other according to an example embodiment of the present invention. FIGS. 2 to 4 are cross-sectional views taken along a line of I-I' of FIG. 1, illustrating steps of connecting the blood vessels via the blood vessel apparatus of FIG. 1.

Referring to FIG. 1 to FIG. 4, the blood vessel apparatus 100 according to the present example embodiment includes an elastic connection part 200 and a fixing part 300.

When a first blood vessel 10 and a second blood vessel 20 are connected each other, the blood vessel connecting apparatus 100 is inserted and placed into an end of the second blood vessel 20. The end of the second blood vessel 20 is inserted into the first blood vessel 10 while the blood vessel connecting apparatus 100 is arranged along an inside wall of the second blood vessel 20.

Here, FIG. 1 merely shows that the end of the second blood vessel 20 is connected to a side wall of the first blood vessel 10. Alternatively, although not shown in the figure, the end of the second blood vessel 20 may be connected to an end of the first blood vessel 10.

Each of the first blood vessel 10 and the second blood vessel 20 may be an artificial blood vessel or a vital blood vessel.

The elastic connection part 200 includes a first support unit 210 and a second support unit 220, and the fixing part 300 includes a first guide unit 310 and a first temporary fixing unit 320.

As a plurality of the elastic connection parts 200 is shown in FIG. 1, the elastic connection parts 200 may be arranged along the inside wall of the second blood vessel 20 and each of the elastic connection parts 200 extending from the inside wall of the second blood vessel 20 to the end of the second blood vessel 20 sharply forms toward the end of the second blood vessel 20. A first end of the elastic connection part 200 is arranged toward the end of the second blood vessel 20 and a second end of the elastic connection parts 200 is arranged toward the inside of the second blood vessel 20.

In addition, the first end of the elastic connection part 200 may bend toward an outside of the end of the second blood vessel 20, and the second end of the elastic connection part 200 may be arranged to the inside of the second blood vessel 20 in a straight line, since the elastic connection part 200 has an elasticity to bend toward the outside of the end of the second blood vessel 20.

Each of the elastic connection parts 200 is spaced apart from each other along the perimeter of the inside wall of the second blood vessel 20 at a predetermined distance and the fixing part 300 fixes the first and second ends of the elastic connection part 200 to the inside wall of the second blood vessel 20, such that each of elastic connection parts 200 forms substantially parallel to the inside wall of the second blood vessel 20.

The first support unit 210 fixed with the inside wall of the second blood vessel 20 is formed at the second end of the elastic connection part 200 inserted into the inside of the second blood vessel 20. The second support unit 220 extending from the first support unit 210 is formed at the first end of the elastic connection part 200 and bends toward the outside of the end of the second blood vessel 20.

The first support unit 210 and the second support unit 220 have the elasticity to bend toward the outside of the end of the second blood vessel 20, and the first guide unit 310 is formed between the second support unit 220 and the second blood vessel 20, so that the second support unit 220 is prevented from being bent to the outside of the end of the second blood vessel 20. Thus, the first guide unit 310 at an outside of the second support unit 220 may prevent a plurality of the second support units 220 having a circular shape and arranged at the first end of the elastic connection part 200 from being bent.

The first support unit 210 formed at the second end of the elastic connection part 200 fixes the elastic connection apparatus 200 to the inside wall of the second blood vessel 20 so that a plurality of the first support units 210 is prevented from being bent and is arranged along the inside wall of the second blood vessel 20.

The second support unit 220 simultaneously bends and moves toward the first blood vessel 10, and the first support unit 210 makes contact with the first guide unit 310 and bends to the outside of the end of the second blood vessel 20, when the first temporary fixing unit 320 is removed.

Here, the second support unit 220 simultaneously passes through the first blood vessel 10 and the second blood vessel 20, and bends toward the outside of the end of the second blood vessel 20 and the first support unit 210, so that the first and second blood vessels 10 and 20 are connected with each other and twisted with each other.

Referring to FIG. 4, the second support unit 220 passes through the first blood vessel 10 and the second blood vessel 20, and pulls the first blood vessel 10 to the second blood vessel 20. In addition, the first blood vessel 10 and the second blood vessel 20 are circularly bent and twisted when the second support unit 220 continues to pull the first blood vessel 10 to the second blood vessel 20.

The first support unit 210 and the second support unit 220 connect the first blood vessel 10 to the second blood vessel, and the first blood vessel 10 and the second blood vessel 20 are twisted each other, so that blood is prevented from leaking the outside of the first and the second blood vessels 10 and 20.

In addition, the elasticity of the first support unit 210 and the second support unit 220 puts pressure on the first blood vessel 10 and the second blood vessel 20 to keep the connection between the first blood vessel 10 and the second blood vessel 20, so that a binding force between the first blood vessel 10 and the second blood vessel 20 increases.

In accordance with a specific connection step of the blood vessel connecting apparatus 100, the first support unit 210 and the second support unit 220 in FIG. 2 are inserted into the inside wall of the second blood vessel 20, and the second support unit 220 and the first guide unit 310 may protrude from the end of the second blood vessel 20 or formed at the inside wall of the end of the second blood vessel 20.

The position of the blood vessel connection apparatus 100 in the second blood vessel 20 may be changed according to surgery conditions such as a size of the first blood vessel 10 and a thickness of a wall of the first blood vessel 10 or the second blood vessel 20.

Referring to FIGS. 3 and 4, the end of the second blood vessel 20 is inserted into the side wall of the first blood vessel 10 when the blood vessel connecting apparatus 100 protrudes from the end of the second blood vessel 20 or is inserted into the same. Each of the second support units 220 bends toward an outside of the end of the second blood vessel 20 and passes through the first blood vessel 10, so that the second support unit 220 moves toward the first support unit 210 when the first temporary fixing unit 320 is removed.

Alternatively, the second support unit 220 passes through the inside wall of the second blood vessel 20 and bends toward the outside of the second blood vessel 20 when the second support unit 220 is inserted into the end of the second blood vessel 20. The second support unit 220 passes through the first blood vessel 10 and pulls the first blood vessel 10 to the outside of the second blood vessel 20.

Thus, the second support unit 220 is bending and moving toward the first blood vessel 10 and pulling the first blood vessel 10 to the outside of the second blood vessel 20, so that the blood vessel connecting apparatus 100 may quickly connect the first blood vessel 10 to the second blood vessel 20 and reduce a side-effect of the surgery. Thus, high skill is unnecessary to use the blood vessel connecting apparatus 100.

In addition, the first blood vessel 10 and the second blood vessel 20 make contact with each other and are twisted with each other, so that the blood inside of the first and second blood vessels 10 and 20 is prevented from leaking outside of the first and second blood vessels 10 and 20 and the binding force between the first blood vessel 10 and the second blood vessel 20 increases via the pressure generated from the elasticity of the second support unit 220.

In addition, the first guide unit 310 is arranged between the first support unit 210 and the second blood vessel 20 and prevents the first support unit 210 from rapidly bending and moving toward an unintended direction when the first temporary fixing unit 320 is removed and the first support unit 210 and the second support unit 220 simultaneously bend to the outside of the second blood vessel 20.

Figure 5:
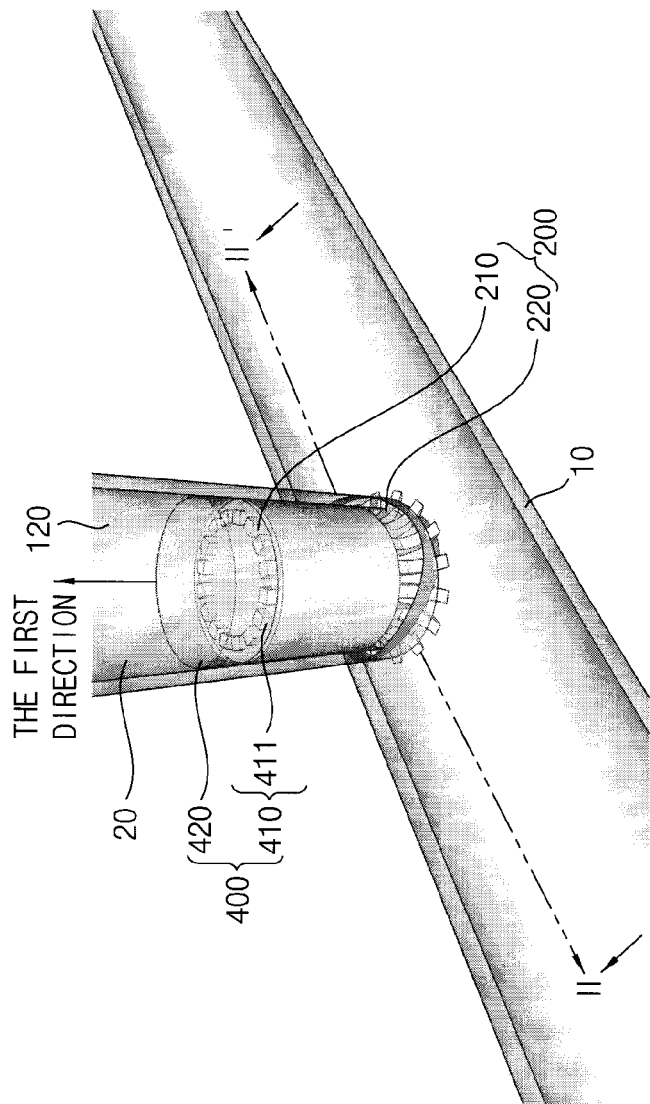
FIG. 5 is a perspective view illustrating a blood vessel connecting apparatus according to another example embodiment of the present invention.
Figure 6:
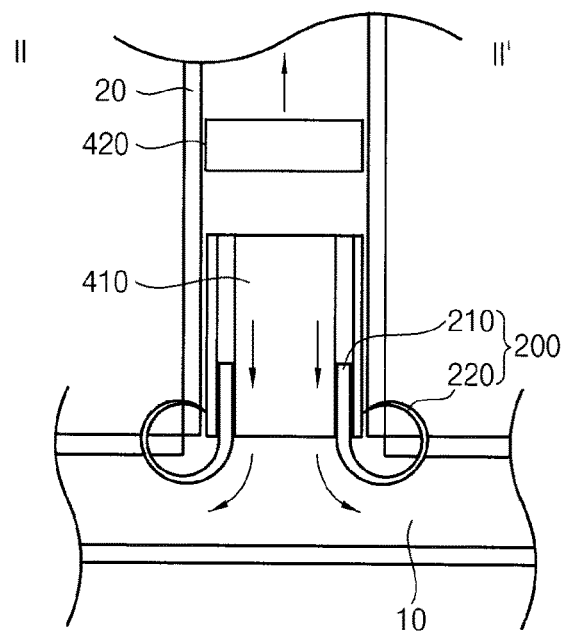
FIGS. 6 and 7 are cross-sectional views taken along a line of II-II' of FIG. 1, illustrating steps of connecting the blood vessels via the blood vessel apparatus of FIG. 5.
Figure 7:
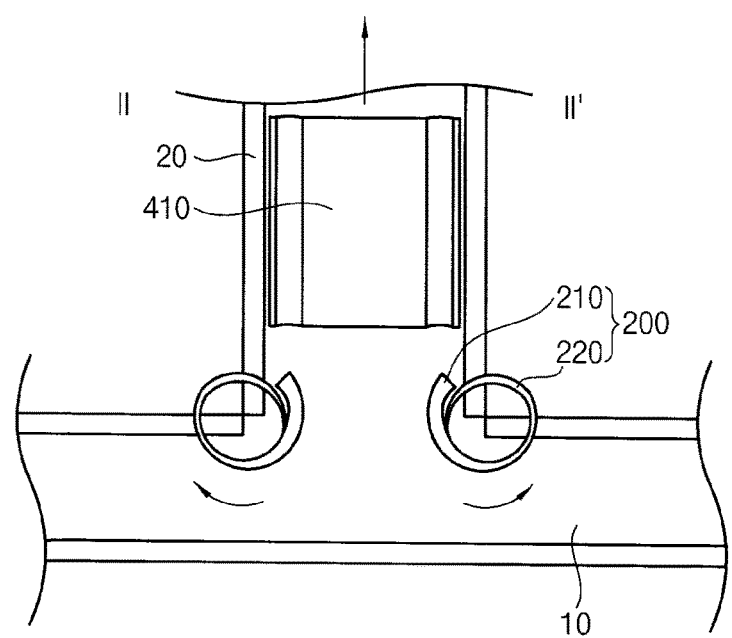
Figure 8:
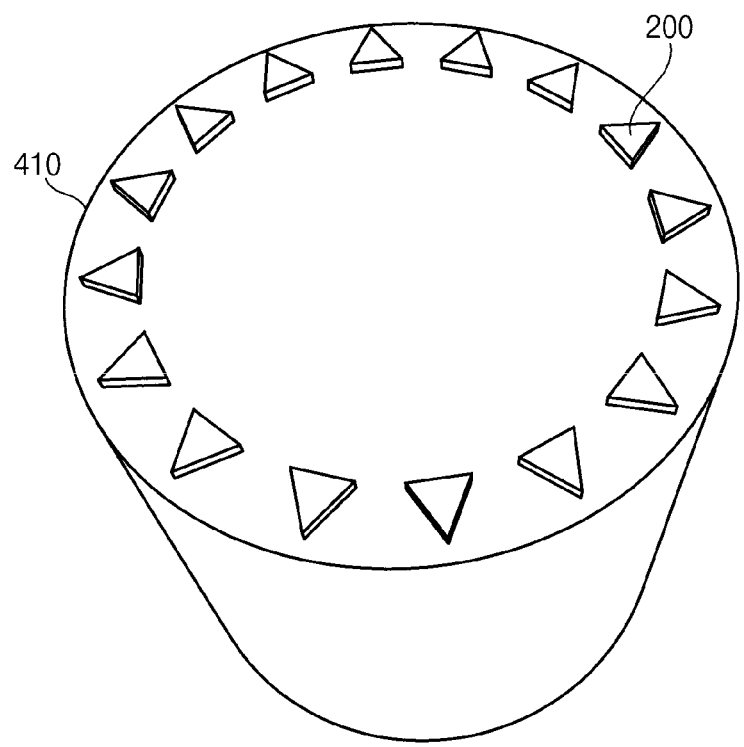
FIG. 8 is a perspective view of illustrating an example of a second guide unit and an elastic connection part.

FIG. 5 is a perspective view illustrating a blood vessel connecting apparatus according to another example embodiment of the present invention. FIGS. 6 and 7 are cross-sectional views taken along a line of II-IF of FIG. 1, illustrating steps of connecting the blood vessels via the blood vessel apparatus of FIG. 5. FIG. 8 is a perspective view of illustrating another example of the second guide unit and an elastic connection part of FIG. 5.

The blood vessel connecting apparatus 120 according to the present example embodiment is substantially same as the blood vessel connecting apparatus 100 in FIGS. 1 to 4, and same reference numerals are used and any repetitive explanation will be omitted.

Referring to FIG. 5 to FIG. 8, the blood vessel connecting apparatus 120 according to the present example embodiment includes a fixing part 400.

The fixing part 400 includes a second guide unit 410 and a second temporary fixing unit 420, and the second guide unit 410 includes an inserting part 411.

The second guide unit 410 has a cylindrical shape, and the first support unit 210 is inserted into the inserting part 411 extending from a top surface of the second guide unit 410 to the first blood vessel 10. A plurality of the inserting parts 411 is arranged along the edge of the second guide unit 410.

The first support unit 210 is inserted into the inserting part 411 arranged along the edge of the second guide unit 410, so that the first support unit 210 forms straight in the second blood vessel 20. The second support unit 220 may be inserted into the second guide unit 410 or a portion of an end of the second support unit 220 may protrude into the first blood vessel 10.

The first support unit 210 keeps straight in the inserting part 411 under the control of the elasticity thereof. The second support unit 220 protrudes from the end of the second blood vessel 20 and an outside of the inserting part 411, and bends to the outside of the end of the second blood vessel 20.

As shown in FIG. 6, the second temporary fixing unit 420 is arranged at an upper side of the second guide unit 410 and connected to the first support unit 210, so that the first support unit 210 is prevented from being detached from the second guide unit 410.

The second guide unit 410 moves toward the second blood vessel 20 and the first support unit 210 starts to move away from the inserting part 411, when the second temporary fixing unit 420 is detached from the first support unit 210.

In addition, the second support unit 220 moves toward the first blood vessel 10 and bends, so that the second support unit 220 passes through the first blood vessel 10 and the second blood vessel 20.

Here, the second guide unit 410 is fixed in the second blood vessel 20 and the inserting part 411 makes contact with the first support unit 210. The second support unit 220 stably bends toward the outside of the second blood vessel 20 while the first support unit 210 is spaced apart from the inserting part 411.

A plurality of the second support units 220 is arranged along the end of the second blood vessel 20 and is spaced apart from each other at a predetermined distance. Thus, when a plurality of the second support units 220 passes through the first blood vessel 10 and the second blood vessel 20 and bends, the first blood vessel 10 is stably connected to the second blood vessel 20.

For example, the connection between the first blood vessel 10 and the second blood vessel 20 loosens and thus the blood in the second blood vessel 20 may leak out, when some of a plurality of the elastic connection parts 200 are bending toward a random direction and are arranged along the end of the second blood vessel 20 at an irregular distance.

As shown with an arrow in FIG. 6, the surgery takes the second guide unit 410 out to a first direction in the second blood vessel 20 after the elastic connection part 200 is spaced apart from the second guide unit 410 and connects the second blood vessel 20 to the first blood vessel 10.

Thus, while the second temporary fixing unit 420 is spaced apart from the second guide unit 410 and the first support unit 210 moves to the first blood vessel 10, the second guide unit 410 guides a bending direction of the elastic connection part 200 so that the first blood vessel 10 is strongly connected with the second blood vessel 20.

In addition, a shape of the inserting part 411 may be changed according to a shape of the elastic connection part 200 or a condition of a blood vessel. Various kinds of the elastic connection part 200 may be used to minimize a wound during the surgery and adapt a size of the first blood vessel 10 and the second blood vessel 20.

For example, a wound generated from the first support unit 210 and the second support unit 220 may be reduced, when the shape of the elastic connection part 200 has a concave shape in a direction of an outside of the second guide unit 410 and has a swollen shape in a direction of an inside of the second guide unit 410. The concave shape of the elastic connection part 200 matches with the swollen shape of the elastic connection part 200 when the second guide unit 410 is removed and the elastic connection part 200 bends.

In addition, the first support unit 210 is inserted into an inside of the inserting part 411 and the first support unit 210 is prevented from bending in the inserting part 411.

In addition, the second guide unit 410 guides the first support unit 210 to bend the outside of the end of the second blood vessel 20 before the second guide unit 410 is spaced apart from the first support unit 210.

Accordingly, the blood vessel connecting apparatus 100 is inserted into an first end of the second blood vessel 20 and a portion of the first end of the second blood vessel 20 is inserted into the inside of the first blood vessel. Then, the first support unit 210 and the second support unit 220 quickly bend to the outside of the end of the second blood vessel 20, and the first support unit 210 moves toward the first blood vessel 10, when the first temporary fixing unit 320 is removed. Thus, the elasticity of the first support unit 210 and the second support unit 220 provides force to connect the second blood vessel 20 to the first blood vessel 10. In addition, the side-effects of the surgery may be reduced and the blood vessel connecting apparatus 100 doesn't require relatively high skill for use.

In addition, the first blood vessel 10 and the second blood vessel 20 are connected and twisted with each other and a contact area between the first blood vessel 10 and the second blood vessel 20 increases, so that the contact area prevents the blood from leaking out from the first blood vessel 10 and the second blood vessel 20 and a binding force between the first blood vessel 10 and the second blood vessel 20 increases via the elasticity of the second support unit 220.

In addition, the first guide unit 310 is arranged between the first support unit 210 and the second blood vessel 20 and prevents the elastic connection part 200 from bending drastically and from moving to an unintended direction, when the first temporary fixing unit 320 is removed and the first support unit 210 and the second support unit 220 simultaneously bend.

In addition, the inserting part 411 makes contact with the first support unit 210 to guide the second support unit 220 to bend toward the outside of the end of the second blood vessel 20 and a plurality of the second support units 220 is spaced apart from each other at a predetermined distance, so that the first blood vessel 10 is strongly connected with the second blood vessel 20.

In addition, the shape of the inserting part 411 may be changed depending on the shape of the elastic connection part 200 or the condition of the first blood vessel 10 and the second blood vessel 20, and may minimize the wound of the first blood vessel 10 and the second blood vessel 20.

The foregoing is illustrative of the present teachings and is not to be construed as limiting thereof. Although a few exemplary embodiments have been described, those skilled in the art will readily appreciate from the foregoing that many modifications are possible in the exemplary embodiments without materially departing from the novel teachings and advantages of the present disclosure of invention. Accordingly, all such modifications are intended to be included within the scope of the present teachings. In the claims, means-plus-function clauses are intended to cover the structures described herein as performing the recited function and not only structural equivalents but also functionally equivalent structures.

What is claimed is:

1. An artificial blood vessel connecting apparatus configured to connect a first artificial blood vessel to a second artificial blood vessel, the artificial blood vessel connecting apparatus comprising:
   an elastic connection part having an elastic restoring force, and comprising a first support unit and a second support unit,
      the first support unit configured to be inserted inside the second artificial blood vessel,
      the second support unit extending from the first support unit to an end of the second artificial blood vessel, wherein an end of the second support unit is sharply formed; and
   a fixing part comprising:
      a temporary fixing unit temporarily fixing the first support unit, and
      a guide unit configured to be fixed inside the second artificial blood vessel, and configured to be formed between the second artificial blood vessel and the second support unit,
   wherein the guide unit is disposed closer to the first artificial blood vessel than the temporary fixing unit,
   wherein the temporary fixing unit is separated from and spaced apart from the guide unit by a predetermined distance, and the temporary fixing unit is disposed between the first support unit and the second artificial blood vessel, wherein, in response to the temporary fixing unit being detached and removed away from the first artificial blood vessel, the first and second support units simultaneously move forward towards the end of the second artificial blood vessel and bend, so that the first and second support units connect the first artificial blood vessel to the second artificial blood vessel, wherein the guide unit is fixed to an inside wall of the end of the second artificial blood vessel, and does not protrude into the first artificial blood vessel while the first and second support units simultaneously move and bend, and wherein the elastic connection part is initially disposed inside of the second artificial blood vessel, so that the second support unit moves from an inside of the first artificial blood vessel toward an outside of the first artificial blood vessel, then through the second artificial blood vessel, and back towards the inside of the first artificial blood vessel when the first and second units start to connect the first artificial blood vessel to the second artificial blood vessel.

2. The artificial blood vessel connecting apparatus of claim 1, comprising a plurality of elastic connection parts disposed along a perimeter of the second artificial blood vessel, wherein the fixing part fixes the elastic connection parts, so that the elastic connection parts are spaced apart from each other at a predetermined distance along the perimeter of the second artificial blood vessel.

3. The artificial blood vessel connecting apparatus of claim 2, wherein in response to the temporary fixing unit being detached and removed from the elastic connection parts, each of the elastic connection parts simultaneously moves toward the first artificial blood vessel and bends via the elastic restoring force, so that the elastic connection parts connect the first artificial blood vessel to the second artificial blood vessel.

4. The artificial blood vessel connecting apparatus of claim 3, wherein each of the elastic connection parts further simultaneously passes through the first and second artificial blood vessels and bends, so that the first and second artificial blood vessels are twisted with each other.

5. The artificial blood vessel connecting apparatus of claim 1, wherein the guide unit has a cylindrical shape, a first end of the guide unit is inserted into the second artificial blood vessel, and a second end of the guide unit is exposed at the end of the second artificial blood vessel.

6. The artificial blood vessel connecting apparatus of claim 5, wherein the guide unit comprises an inserting part extending from the first end of the guide unit to the second end of the guide unit, and the first support unit is inserted into the inserting part and makes close contact with the inserting part.

7. An artificial blood vessel connecting apparatus, comprising:

a first artificial blood vessel and a second artificial blood vessel;

an elastic connection part having an elastic restoring force, and comprising a first support unit and a second support unit, the first support unit is inserted inside the second artificial blood vessel, the second support unit extending from the first support unit to an end of the second artificial blood vessel, wherein an end of the second support unit is sharply formed; and a fixing part comprising:

a temporary fixing unit temporarily fixing the first support unit inside the second artificial blood vessel, and a guide unit fixed inside the second artificial blood vessel, and between the second artificial blood vessel and the second support unit, wherein the guide unit is disposed closer to the first artificial blood vessel than the temporary fixing unit, wherein the temporary fixing unit is separated from and spaced apart from the guide unit by a predetermined distance, and the temporary fixing unit is disposed between the first support unit and the second artificial blood vessel, wherein, in response to the temporary fixing unit being detached and removed away from the first artificial blood vessel, the first and second support units simultaneously move forward towards the end of the second artificial blood vessel and bend, so that the first and second support units connect the first artificial blood vessel to the second artificial blood vessel, and wherein the guide unit is fixed to an inside wall of the end of the second artificial blood vessel, and does not protrude into the first artificial blood vessel while the first and second support units simultaneously move and bend, wherein the elastic connection part is initially disposed inside of the second artificial blood vessel, so that the second support unit moves from an inside of the first artificial blood vessel toward an outside of the first artificial blood vessel, then through the second artificial blood vessel, and back towards the inside of the first artificial blood vessel when the first and second units start to connect the first artificial blood vessel to the second artificial blood vessel.

8. The artificial blood vessel connecting apparatus of claim 7, comprising a plurality of elastic connection parts disposed along a perimeter of the second artificial blood vessel, wherein the fixing part fixes the elastic connection parts, so that the elastic connection parts are spaced apart from each other at a predetermined distance along the perimeter of the second artificial blood vessel.

9. The artificial blood vessel connecting apparatus of claim 8, wherein in response to the temporary fixing unit being detached and removed from the elastic connection parts, each of the elastic connection parts simultaneously moves toward the first artificial blood vessel and bends via the elastic restoring force, so that the elastic connection parts connect the first artificial blood vessel to the second artificial blood vessel.

10. The artificial blood vessel connecting apparatus of claim 9, wherein each of the elastic connection parts further simultaneously passes through the first and second artificial blood vessels and bends, so that the first and second artificial blood vessels are twisted with each other.

11. The artificial blood vessel connecting apparatus of claim 7, wherein the guide unit has a cylindrical shape, a first end of the guide unit is inserted into the second artificial blood vessel, and a second end of the guide unit is exposed at the end of the second artificial blood vessel.

12. The artificial blood vessel connecting apparatus of claim 11, wherein
the guide unit comprises an inserting part extending from the first end of the guide unit to the second end of the guide unit, and
the first support unit is inserted into the inserting part and makes close contact with the inserting part.

* * * * *